United States Patent [19]

Gregor et al.

[11] Patent Number: 4,705,753

[45] Date of Patent: Nov. 10, 1987

[54] BIOLOGICALLY ACTIVE ACRYLONITRILE-BASED COPOLYMERIC MEMBRANE

[76] Inventors: Harry P. Gregor, 410 Riverside Dr., New York, N.Y. 10025; Paul I. Dalven, 28/08 Chatam Sofer St., A'manuel 90943, Israel; James R. Hildebrandt, 560 Riverside Dr., New York, N.Y. 10027; Leonard T. Hodgins, 19 Jane St., Closter, N.J. 07624; Anthony J. Laccetti, 60 Haven Ave., New York, N.Y. 10032; Abraham Shamir, 530 West 113th St., New York, N.Y. 10025

[21] Appl. No.: 618,652

[22] Filed: Jun. 8, 1984

[51] Int. Cl.$^4$ .................. C12N 11/08; C12N 11/06; C12N 11/00; G01N 33/545

[52] U.S. Cl. .................. 435/180; 435/174; 435/181; 436/531; 436/532; 530/815; 530/816

[58] Field of Search .................. 436/531, 532, 828; 435/174, 180, 181, 188, 14, 213, 262, 269, 272; 525/50, 54.1; 521/53, 64; 530/815, 816

[56] References Cited

U.S. PATENT DOCUMENTS

| | | | |
|---|---|---|---|
| 3,808,305 | 4/1974 | Gregor | 264/331.12 |
| 3,834,990 | 9/1974 | Werle et al. | 435/213 X |
| 3,939,041 | 2/1976 | Lartigue et al. | 435/174 X |
| 3,964,973 | 6/1976 | Hradil et al. | 435/181 X |
| 4,033,817 | 7/1977 | Gregor | 435/44 |
| 4,352,884 | 10/1982 | Nakashima et al. | 435/180 |
| 4,371,612 | 2/1983 | Matsumoto et al. | 435/44 |

OTHER PUBLICATIONS

Miekka et al., "Chem. Abstracts", vol. 97, (1982), Abstract #133409q.

*Primary Examiner*—David M. Naff
*Attorney, Agent, or Firm*—Sprung Horn Kramer & Woods

[57] ABSTRACT

A membrane is produced by dissolving, in a water-miscible solvent, a water insoluble copolymer of acrylontrile with at least one monomer selected from the group consisting of an aminostyrene, a vinyl pyridine and an N-hydroxy-containing-substituent-acrylamide, casting said solution to form a thin layer of solution, contacting said solution with water thereby to coagulate the copolymer into a film, and washing away from the copolymer film the solution of solvent and water. The amine or hydroxy group of the copolymer is then activated and coupled with a ligand such as glucose isomerase, chymotrypsin or Protein A. The coupled membranes can then be used for biological separations and reactions.

9 Claims, No Drawings

BIOLOGICALLY ACTIVE ACRYLONITRILE-BASED COPOLYMERIC MEMBRANE

BACKGROUND OF THE INVENTION

The present invention relates to the preparation of membranes and their use in effecting enzymatic and biological reactions and separations.

The present invention encompasses a group of matrix membranes, coupling reactions, proteins, enzymes and antibodies, in some respects similar to those of U.S. Pat. Nos. 4,0333,817, 4,033,822 and 4,863,714. As there, there are provided membrane filters to which enzymes and other molecules of similar catalytic or binding activity are attached via chemical bonds, where activation of the pore surfaces of these membranes or filters for purposes of subsequent coupling (where such is needed) can be carried out under pressure-driven conditions, and where the resulting coupled enzyme or biopolymer system can be used under pressure-driven conditions, i.e., by forcing the substrate to be treated through the membrane pores under pressure, to effect useful conversions and separations.

The conventional uses of immobilized biopolymers are well-known in the scientific, industrial and patent literature. The advantages of the immobilization procedure are well-known. The technologies which are usually employed have involved the use of fine particles of either natural or synthetic materials, often of organic polymers or porous materials of other substances, to which enzymes, proteins and other biopolymers are coupled by chemical bonds. These conventional processes have advantages and various disadvantages.

Further, membranes composed of natural polymers such as cellulose or of proteins have been employed, but these are susceptible to degradation or attack by microorganisms and enzymes. A number of purely synthetic membranes have been employed as carriers for protein immobilization, but these are usually not porous membranes but rather in the form of sheets coated with coupling groups, or systems where the active agent such as an enzyme fills the pores and process rates are diffusion-controlled, in large measure.

Still further, polymers of acrylonitrile (PAN) have seldom found use for enzyme immobilization. Where they have, it was under conditions which presented many problems of a preparative nature or in use. For example, proteins have been ionically bound to an acrylonitrile homopolymer after partial derivatization of the nitrile groups to imidoesters; however, only a small amount of protein could be bound. Similarly, amine monomers can be grafted onto PAN polymerized in the presence of bromoform, e.g., the photografting of N,N-dimethylaminoethyl methacrylate, followed by quaternization of the amine and then used via the process of ionic immobilization for the enzyme urease. Further, one can introduce amines into PAN by partial reduction of the nitrile groups; this facilitates the adsorption of proteins which can then be subsequently cross-linked with gluteraldehyde into a stable network. Such supports, however, have limited utility because the activation/coupling chemistries are not versatile and the process results in weak chemical bonds which cannot prevent enzyme leakage due to solvolytic processes.

It is accordingly an object of the present invention to provide ways of immobilizing biopolymers so that they can still engage in biological reactions and interactions to substantially the same extent as the mobile biopolymers prior to immobilization.

It is a further object of the invention to provide a way of producing from acrylonitrile polymers which in membrane form have high versatility and utility.

These and other objects and advantages are realized in accordance with the present invention pursuant to which there are provided novel methods of preparing such membranes, improvements in the coupling chemistries which are employed, and the use of these systems for specific applications of value. Where the system is used as a catalyst for the carrying out of a specific chemical reaction such as the isomerization of glucose, in the manner as described hereinbelow, the system displays a high capacity in terms of its enzyme content and, accordingly, a high enzymatic activity, making this system useful for the large-scale industrial process of glucose isomerization. Enzymes so stabilized have, in addition to the above-mentioned advantages, an intrinsic advantage in terms of a high chemical and thermal stability.

Similarly, when to these membrane filters or ultrafilters are coupled specific ligands, namely substances capable of forming specific complexes with certain species present in a mixture with other substances which may be similar in nature, where the specific agents and ligands are attached by chemical bonds to the inner pore surface of the membrane under pressure-driven conditions, then a process termed affinity sorption, as described in U.S. Pat. No. 4,163,714 can take place, similar to the well known process of affinity chromatography, but possessing unique advantages of speed and convenience. In affinity sorption, the pore diameters and chemical nature of these membranes must be such as to allow for the coupling of a high concentration of ligand, and also to provide for the ready access of the solute molecules whose separation and purification via reversible binding to the ligand substances is desired. The nature of these membranes is such that the excess, undesired components of the mixture can readily be washed out of the membrane or filter under pressure-driven conditions, and then the complex can be dissociated and the desired substance displaced with the effluent in a pure and concentrated state.

Thus, this invention provides new and advantageous ways of effecting separations for analytical and preparative purposes and can be compared with the conventional process of affinity chromatography. Specific advantages of these pressure-driven affinity sorption systems are further set forth in U.S. Pat. No. 4,163,714.

SUMMARY OF THE INVENTION

In accordance with the present invention, we have found that membranes of high capacity, stability and suitability for the binding of various kinds of enzymes and biopolymers can be prepared as is subsequently described.

Specifically, there is provided a series of ultrafiltration membranes based upon synthetic copolymers "tailor made" for specific types of enzyme and protein coupling reactions. The predominant monomer of these copolymers is acrylonitrile (AN) which is the basis for an excellent film-forming polymer, and which can be copolymerized with a wide variety of comonomers. These comonomers include those containing an aryl amine (an amino styrene), a vinyl pyridine or a hydroxyl-containing olefin, e.g., an N-hydroxy-containing-substituent-acrylamide. These can be readily copolymerized with AN and then employed in a variety of activation/coupling chemistries.

The copolymers are dissolved and cast into sheet-like films or as coatings onto particulate matter such as beads, fibers, etc. Then the copolymer is coagulated, i.e., insolubilized. The amine or hydroxy groups are thereafter activated and bound to ligands, enzymes or other biological molecules so as to be capable of use in biological reactions and interactions.

The copolymers, upon coagulation, are in the form of membranes, either sheet-like in the conventional manner or as thin coatings on a carrier. The sizes of the enzyme or biopolymer molecules being coupled to the membranes must be matched to the size of the membrane pores. The size of enzymes and biopolymers can be determined by many techniques, of which calculations based upon the rates of diffusion are but one. The size of the membrane pores is usually determined by the measurement of the relative rates of diffusion or filtration of molecules of a different size. Here, the use of dextran molecules of different sizes is particularly useful. We have found that simple mechanical models suffice as a guide for the preparative procedures used in making the membranes and filters. In effect, the walls of the membranes or filters are lined with enzyme or biopolymer by pumping in solutions thereof from one side of the membrane to the other, after suitable activation. Pores will be blocked unless the pore diameter is at least three times that of the enzyme, protein or antibody. If the feed material contains particularly large molecules which must pass for the purpose of separation or attachment, then membrane diameters considerably larger may be required. One of the important considerations in this invention is the ability to make systems of a specific pore size to fit a specific application.

In order to make use of the pressure-driven concept and where a high capacity is desired, it is important also that the matrix membrane or filter has pores of molecular dimensions so that the system can have a high internal surface for coupling. Membranes having pores of the dimensions of microns are not generally as useful in this regard. The high capacity membranes of this invention usually have pores with diameters ranging from approximately 20 to 200 nm. The matrix membrane must also be capable of withstanding a suitable pressure gradient across it of at least 10 psi on the average, and also be stable at the operating temperature of the system.

Such acrylonitrile copolymeric membranes have found application in certain processes of catalysis, namely conversion of glucose to fructose by an isomerase, as well as in certain areas of separation and purification wherein the affinity sorption principle is used, namely in the removal of desirable substances as part of the fractionation of blood, as well as in affinity sorption as in the separation and purification of antibodies (including monoclonal antibodies) and the parallel use of bound antibodies in affinity sorption processes. The polymers of this invention are usually employed in the form of ultrafiltration membranes but they can also be employed in the form of microporous filters where large pore diamters are needed and a lower capacity is allowed. These polymers can also be used to coat surfaces where a surface reaction suffices for the application.

DETAILED DESCRIPTION OF THE INVENTION

Various high molecular weight copolymers of acrylonitrile and a vinyl comonomer containing an aryl amine, a pyridine, or an aliphatic hydroxyl group have been synthesized via slurry polymerization techniques so as to contain from about 1 to 15 mole percent of functional comonomer.

The teachings of this invention are applicable to a wide range of distinct copolymers of acrylonitrile which can be synthesized to contain one of three different types of functional comonomers. The functional comonomer contained can be either an aryl amine (mAS, pAS), a pyridine (4VP, PEAM), or a hydroxyl group (HOPAM, HOPMAM, HDNMAM). The examples give details of the preparative procedures. Each type of comonomer permits a different activation/coupling chemistry for protein-ligand immobilization.

A variety of factors are involved in choosing a comonomer, the comonomer concentration in the feed, and the polymerization conditions. Considerations include monomer reactivity ratios, availability of comonomers, stability of comonomers and copolymers, copolymer hydrophilicity, as well as the steric availability, the distance of a functional group from the backbone chain of the copolymer. Overriding these considerations in the design of a synthesis, however, is the copolymer's performance in making a membrane of suitable physical/structural stability with the desired porosity. This, in turn, requires producing a polymer of sufficiently high molecular weight without conconmittant gel formation or post-polymerization crosslinking.

For hydroxyl-containing copolymers, the methacrylamide derivatives were found to be superior to the acrylamides. Besides having more favorable reactivity ratios, the methacrylamides gave fewer problems with crosslinking and polymer gelation after dissolution in DMF. Of the two methacrylamides, HDNMAM is a more hydrophilic copolymer than HOPMAM; in addition, the increased length of the spacer arm in HDNMAM is a desirable feature for protein immobilization. However, there is a tendency for a crosslinked gel to form during the polymerization with HDNMAM as compared with the formation of a crystalline glass-like polymer in the syntheses with HOPMAM. This limitation can be overcome by maintaining a low feed concentration of methacrylamide, such as—2 mole % HDNMAM and—5 mole % HOPMAM.

Estimates of the molecular weight of several copolymers can be made from intrinsic viscosity measurements. Such estimates are useful when polymerization conditions need to be adjusted to result in the synthesis of a copolymer with viscosity in DMF appropriate for membrane casting. Since a definite measurement of the molecular weight is not required, concentration terms of order two and higher can be ignored. The dependence of the intrinsic viscosity upon the molecular weight of the copolymer can be assumed to be identical to that of a homopolymer of acrylonitrile.

The intrinsic viscosity of the copolymers in DMF ranged from 89.8 to 298 ml/g, depending on the particular polymerization conditions. Such intrinsic viscosities correspond to a weight-average molecular weight range of 60,000 to 300,000. Copolymers with an intrinsic viscosity of 120 to 200 ml/g were found to be the most suitable for the casting of unsupported membranes of the requisite physical stability and of the desired water permeability.

The copolymer composition can be estimated by UV spectroscopy with the monomer extinction coefficient used as a reference. By UV, the mole ratio mAS/AN in the copolymers is estimated to be about 1.5 times that in the feed. For example, syntheses in which the mole % of mAS in the feed varied from 1.0 to 5.0 resulted in copolymers with a mAS content of 1.8 to 8.5 mole %. The mole content of pAS in the polymer was always less than that in the feed by a factor of about 2 to 3. A feed with 5.0 mole % pAS resulted in a copolymer with 1.9 mole % pAS. Since high molecular weight copolymers of pAS and acrylonitrile are difficult to obtain under the given synthetic conditions, most of the protein immobilizations utilized mAS copolymers.

Syntheses containing from 2.5 to 15 mole % 4VP in the feed resulted in copolymers containing from 3.0 to 20.5 mole % 4VP, respectively. The incorporation levels of 4VP are consistent with the reactivity ratios previously reported.

Acid-base titrations of copolymers containing pyridine or aryl amine functional groups were performed in DMF. The base DTG, when dissolved in DMF, was suitable for the titration of perchlorate copolymer salts.

Acid-base titrations gave, as a rule, a lower comonomer ratio than the UV analysis for the active group. For example, an acrylonitrile-pAS copolymer with 5 mole % pAS in the feed gave 0.84 and 1.6 mole % pAS by titration and UV absorbance, respectively. In contrast, an acrylonitrile-4VP copolymer that contained 10 mole % 4VP in the feed gave 11.7 mole % by acid-base titration and 8.4 mole % by UV absorbance. Such discrepancies may arise from several sources. For example, titration with base may underestimate the true number of functional moieties in a polymer due to the loss of perchlorate during the rigorous washing and drying of the polymer acid salt. On the other hand, estimates based on the UV absorbance are likely to be in error largely due to the assumption of a linear relationship between chromophore concentration and molar extinction coefficient.

The comonomer content can also be quantitated by relative chemical reactivity with trichloro-s-triazine. Films were cast from copolymer solutions, coagulated into unsupported and supported ultrafiltration membranes, and characterized with respect to both water permeability and pore size distribution, the latter by size exclusion chromatography of the membrane permeate of a pool of dextran fractions. These ultrafiltration membranes can be used for protein immobilization after appropriate chemical activation. The three distinct types of functional copolymers give comparable results for alpha-chymotrypsin, as an example, with protein weight loadings of 6 to 12 percent and 40 to 65% retention of enzymatic specific activity.

The invention will be further described in the following illustrative examples wherein all parts are by weight unless otherwise expressed.

The following chemicals were purchased from Aldrich Chemical Co. and the abbreviations have the indicated meanings: 3-(a-hydroxyethyl)aniline (HEA), 4-(2-aminoethyl)pyridine, 4-ethylpyridine, m-ethylaniline, p-ethylaniline, acryloyl chloride, methacryloyl chloride, 2,6-di-tert-butyl-4-methylphenol (BHT), trichloro-s-triazine (TsT), N,N-diisopropylethylamine (DIPEA) and 1,3-di-O-tolylguanidine (DTG). Acrylonitrile, 2,2'-azobis(2-methylpropionitrile) (AIBN) and p-methoxyphenol (MEHQ) were obtained from Eastman Kodak Co. Other chemicals and their vendors include: alumina F1, 14–28 mesh (Alcoa Chemical); N,N-di-2-naphthyl-p-phenylene diamine (Pfaltz & Bauer); N-(9-hydroxy-4,7-dioxa-nonyl)amine (polyglycolamine H-163, from Union Carbide); triethylamine, acetic anhydride, ethylenediamine (EDA), ethylene carbonate (EC), propylene carbonate (PC), N,N-dimethylformamide (DMF), and cyanogen bromide (Fisher Scientific); acrylic acid (Dow Badische Chemical Co.); polyacrylonitrile, (PAN, type A homopolymer, from DuPont); 2-(2-aminoethoxy)ethanol (diglycolamine, from Texaco Chemical Co.); 4-vinylpyridine (4-VP, from Reilly Tar & Chemical Co.); p-aminostyrene (pAS, from Fairfield Chemical Co.); and, Amberlite IRA-900 and IRC-50 (Rohm & Haas). Bovine a-chymotrypsin (CT), blue dextran, e-amino-n-caproic acid (EACA), glutaryl-L-phenylalanine-p-nitroanilide (GPNA), and dextran fractions of average molecular weight 10,500, 17,700, 40,000, 70,300, 252,000, and 2,000,000 were supplied by Sigma Chemical Co. A dextran fraction of molecular weight 4,000 to 6,000 was obtained from Accurate Chemical. Polystyrene calibration standards were the products of Waters Associates or Polysciences Inc. Acrylonitrile (AN) was freshly distilled before use after being made acidic with phosphoric acid.

Also from Aldrich was purchased 2-methoxy-4,6-dichloro-s-tsiazine (MDsT). Glucose isomerase (GI) was obtained from Miles-Kali Chemie.

Also obtained were *Staphylococcus aureus* (Cowan strain) protein A (PA), protein A-Sepharose CL-4B, bovine serum albumin (BSA), bovine alpha-chymotrypsin (CT), glutaryl-L-phenylalanine-p-nitroanilide (GPNA) and globulin-free human serum albumin (HSA) from Sigma Chemical Co; soybean trypsin inhibitor (STI) from Worthington Biochemicals; human immunoglobulin G (IgG) and medium electroendosmosis agarose from Miles Laboratories; Rabbit anti-human serum albumin antisera (anti-HSA qG) was obtained from Cappel Laboratories or Miles Laboratories.

Certain abbreviations are employed in this invention to refer to certain materials. For example, the polymer of AN is referred to as PAN, while the copolymer of AN and m-aminostyrene is referred to as P(AN-mAS).

EXAMPLE 1

Synthesis of m-aminostyrene (mAS).

mAS was prepared by a protocol modified from one for pAS. HEA (50 g) was melted at 80° C. and added dropwise to 50 ml of solid alumina granules heated to about 300° C., 12 torr, in a 3-neck round bottom flask equipped with a heated addition funnel, a thermometer, and a water condenser/receiving flask; the receiving flask contained 3.5 mg of the non-volatile polymerization inhibitor, N,N-di-2-naphthyl-p-phenylene diamine. Care was taken to avoid an excessive rise in temperature during the addition of HEA onto the alumina. The product was removed from the starting material, inhibitor, and water by vacuum distillation at 20 torr through a Vigreaux column. The colorless product in a 50% yield was collected at 54° C. and stored at −20° C. Reverse phase ion-pair chromatography on a Sperisorb-C6 column showed that over 98% of the material absorbing at 280 nm eluted in one peak, with only a minor non-absorbing peak as detected by refractometry.

EXAMPLE 2

Synthesis of
N-(5-hydroxy-3-oxa-pentyl)methacrylamide
(HOPMAM), N-(5-hydroxy-3-oxa-pentyl)acrylamide
(HOPAM), and
N-(9-hydroxy-4,7-dioxa-nonyl)methacrylamide
(HDNMAM).

Three hydroxy-containing vinyl monomers were synthesized by minor variations on the following scheme. A mixture of 500 ml absolute ethanol, 1.0 mole (101 g) triethylamine, 0.2 g MEHQ, and 1.0 mole (105 g) diglycolamine (or 1.0 mole, 163 g, polyglycolamine) was dried thoroughly over 3A molecular sieves and filtered through a 0.45 mm cellulose acetate membrane filter into a 3-neck round bottom flask equipped with an addition funnel, thermometer, and a nitrogen inlet. The flask was cooled to −50° C. by immersion in a dry ice/alcohol bath while under a nitrogen atmosphere; 1.0 mole of methacryloyl chloride (105 g) or acryloyl chloride (90.5 g) was then added slowly, accompanied by overhead mechanical stirring. After the temperature was allowed to increase to −20° C., a triethylamine-HCl precipitate was removed by filtration through paper on a jacketed Buchner funnel maintained at −10° C. The filtrate was pooled with a 100 ml −20° C. ethanol wash of the precipitate and passed through an Amberlite IRA-900 column to remove chloride ions. The effluent was checked for the absence of chloride ions with 1% $AgNO_3$ in 1N $HNO_3$. After rinsing the column with ethanol, 0.2 g of MEHQ was added to the column effluent/wash pool which was subsequently concentrated on a rotary evaporator to about 160 g; this concentration step also removed residual triethylamine. The concentrate was diluted with 250 ml of ethanol and repurified by passage through an Amberlite IRC-50 column to remove residual amines. The effluent was pooled with a 250 ml ethanol rinse of the column and, after the addition of 0.2 g MEHQ, it was concentrated and dried under high vacuum. The yield was between 80 and 85% for all three acrylamides.

EXAMPLE 3

Synthesis of N-(2-(4-pyridyl)ethyl)acylamide (PEAM)

This substituted acrylamide was synthesized from acrylic anhydride and 4-(2-aminoethyl)pyridine. Acrylic anhydride was obtained from acrylic acid and acetic anhydride. Synthesis of PEAM was initiated by the slow addition of 0.36 mole (45.0 g) of acrylic anhydride in 50 ml of ethyl ether containing 50 mg of BHT to 0.35 mole (42.76 g) of 4-(2-aminoethyl)pyridine in 150 ml of ethyl ether containing 150 mg of BHT at −55° C., with the formation of a precipitate. The rate of addition was kept sufficiently slow to ensure that the temperature did not exceed −30° C. during the reaction. After removal of the ether by room temperature evaporation, the precipitate was dissolved in 200 ml of methanol and subsequently vacuum distilled. The substituted acrylamide (15% yield) was collected at 170° C., 100 mtorr.

EXAMPLE 4

Copolymerization of Acrylonitrile with N-Substituted Acrylamides, N-Substituted Methacrylamides, or 4-vinylpyridine These copolymerizations were performed as an aqueous slurry at pH 3.2 with a total monomer concentration of 1.4M. The reactions were done under nitrogen in a resin kettle equipped with a turbine stirrer and an internal cooling coil. A reaction was initiated by the addition of ammonium peroxydisulfate (0.02% final concentration) and sodium metabisulfate (0.1% final concentration); the temperature was thermostatted at 50°+0.3° C. An 80% conversion was typically achieved by 2 to 3 hours. The polymer was isolated by vacuum filtration, washed with water (or 1.0M $NH_4OH$ for a pyridine containing copolymer), dispersed in a blender, collected again by filtration, and dried at 50° C. under vacuum.

EXAMPLE 5

Copolymerization of Acrylonitrile with m— or p-Aminostyrene.

Copolymerization was performed in 50% methanol using AIBN as the initiator. For example, 3.0 g pAS was dispersed in 120 ml of water and concentrated HCl was added until the amine dissolved fully. The solution was then treated with activated charcoal to remove colored contaminants. After filtration to remove the charcoal, the pH was adjusted to 1.1 with concentrated HCl, and 125 ml of methanol was added. The solution was transferred to a 3-neck round bottom flask equipped with a subsurface nitrogen inlet, a thermometer, a mechanical stirrer, and a reflux condenser. Distilled acrylonitrile (65 ml, 53 g) and 150 mg AIBN was added with stirring; the system was purged with nitrogen throughout. The temperature was then brought to and maintained at 50° C. The reaction proceeded rapidly and after 20 hours, 50 ml of 50% methanol was added to thin the slurry. After a total of 48 hours, 50 ml of 1.0M $NH_4OH$ was added and the polymer collected by filtration. Following blending in 1.0M $NH_4OH$ and washing with ethanol, the polymer was dried under vacuum at 40° C. A 70% conversion was typical.

To yield a viscosity suitable for membrane casting, polymers can be dissolved in DMF using extensive mixing with a magnetic stirrer; in some cases, mechanical blending may be employed to decrease the viscosity of the polymer solution to a level suitable for casting. After filtration through Whatman #4 paper, thin films can be spread onto dry chromic acid-washed glass plates with an 8 mil (203 mm) gate opening on a casting knife; this, followed by immediate aqueous coagulation at 2° to 5° C., will minimize skin formation. Hydroxyl, aryl amine, and pyridyl polymer films were coagulated in deionized water, 0.1M, HCl, and 0.1M $NH_4OH$, respectively. Polymer solutions can be stored at either ambient temperatures (hydroxyl polymers) or −20° C. (aryl amine and pyridyl polymers). Membrane sheets can be stored in 10 mM HCl, 0.02% $NaN_3$ at ambient temperatures. Care should be taken to minimize the exposure of the amine polymers and membrane sheets to light.

Membrane thickness can be measured with a Peacock dial gauge, while membrane water content can be estimated, after a quick dry-blotting of surface moisture, by weighing, drying in a vacuum oven, and reweighing of the dry membrane. Water flux can be measured at 50 psi (345 kPa) of $N_2$ on 47 mm diameter membrane disks supported by a non-woven, porous poly(ethylene terphtalate) cloth (Hollytex 3396 from Eaton-Dikeman.)

Assuming that a membrane consists of an ensemble of identically sized cylindrical pores and that Poiseuille's law is applicable, an estimate of a membrane's average pore radius is calculated from $$r = (8hlU/pDAK)^{0.5}$$

where,
r=pore radius in cm;
h=solution viscosity in poise;
l=membrane thickness in cm;
U=rate of fluid in ml/min;
p=pressure in atm;
D=void volume of membrane in %;
A=membrane area in cm$^2$; and
K=a units conversion factor of $6.08 \times 10^7$.

Membranes can be cast onto a support such as Hollyex (Eaton-Dikeman) using the same general procedures, and the properties of the final films resemble those of comparably-cast unsupported membranes except that, since the coagulation solvent attacks the cast films from both faces, the pore structures are somewhat different.

Preparation of membranes is illustrated in the following examples:

EXAMPLE 6

Preparation of P(AN-HOPAM Membrane)

P(AN-HOPAM) polymer from Example 2, of intrinsic viscosity 298 ml/g and with a mole ratio of AN:-HOPAM 9:3 in the feed, was dissolved in DMF to concentrations of 6, 9, 12 and 15 w/v%. These were cast at a gate opening of 7 mils onto glass plates and the plates were immediately thereafter immersed in water at room temperature and then further water washed to remove all soluble material. Disks were then cut from the cast sheets and their properties were measured. The results obtained are set forth in Table 1.

TABLE 1

| Properties of P(AN-HOPAM) Membranes | | | | |
|---|---|---|---|---|
| Membrane | 6.0 | 9.0 | 12.0 | 15.0 |
| Thickness (μm) | 92 | 102 | 110 | 112 |
| Percent Solids | 11.3 | 12.9 | 15.1 | 20.1 |
| Dry Weight/Membrane Area (g/m$^2$) | 8.0 | 11.5 | 16.8 | 23.2 |
| Water Permeability (μm sec$^{-1}$ atm$^{-1}$) | 285 | 230 | 95 | 75 |
| Pore Size Radius (nm) | 49.0 | 46.5 | 32.0 | 29.0 |

EXAMPLE 7

Preparation of P(AN-4VP Membranes)

The process of Example 6 was repeated with one of the copolymers of Example 4 of intrinsic viscosity 133 m/g and a mole ratio in the feed of AN:4VP of 90:10. UV absorption gave the composition as a 85:15 mole ratio.

The results obtained are shown in Table 2.

TABLE 2

| Membrane | 7.0 | 9.1 | 11.9 | 14.0 |
|---|---|---|---|---|
| Thickness (μm) | 97 | 98 | 104 | 105 |
| Percent Solids | 9.5 | 11.5 | 15.1 | 17.6 |
| Dry Weight/Membrane Area (g/m$^2$) | 9.2 | 11.7 | 16.1 | 19.4 |
| Water Permeability (μm sec$^{-1}$ atm$^{-1}$) | 925 | 700 | 530 | 295 |
| Pore Size Radius (nm) | 89.5 | 79.0 | 72.5 | 55.0 |

EXAMPLE 8

Preparation of P(AN-mAS Membranes)

The polymer from Example 5 with an intrinsic viscosity of 198 ml/g and a molar ratio in the feed of AN:-mAS of 96:4, was dissolved in DMF to a concentration of 10% w/v and cast as in Example 6, except that the coagulation liquid was 0.1M HCl in water.

Proteins, enzymes, antibodies, and the like, can be covalently attached to membranes after appropriate activation of the functional monomer in each copolymer. Pyridine containing membranes were activated with cyanogen bromide, while aryl amine and hydroxyl containing membranes can be activated with TsT in dioxane. EDA can be coupled to activated hydroxyl containing membranes in dioxane to prevent hydrolysis of triazinyl-chlorides. The amount of EDA coupled to a membrane can be measured by ninhydrin analysis of dried membrane fragments, using EACA as a standard.

The following examples illustrate membrane activation:

EXAMPLE 9

Trichloro-s-Triazine Activation

TsT and MDsT were recrystallized from ligroin and stored in a dessicator protected from light. The activation of the aryl amine P(AN-mAS) from Example 6 membrane with TsT or MDsT was initiated by the passage of 50 ml of 0.1M NH$_4$OH, followed by placing the membrane in a filtration funnel and passage therethrough of two successive 100 ml portions of 99% p-dioxane, and finally of 25 ml of 0.05M TsT or MDsT in p-dioxane supplemented with 0.1M DIPEA. The membrane was then removed from the filtration funnel and gently stirred in 75 ml of the same solution for 30 to 45 minutes at ambient temperature. Each activated membrane was subsequently soaked for 10 minutes in p-dioxane, remounted in the filtration funnel and flushed successively with 50 ml of p-dioxane and 50 ml of acetonitrile. Displacement of dioxane (m.p 11.8° C.) by acetonitrile was necessitated by the low temperature of the subsequent protein coupling reactions.

EXAMPLE 10

Diazotization of Aryl Amine Membranes

The conversion of the aryl amine membrane of Example 8 to a diazonium salt was effected under N$_2$ pressure by passage through the membrane, in a filtration funnel, of 25 ml of ice-cold 0.5M acetic acid followed by 25 ml of ice-cold 0.3M NaNO$_2$ in 0.5M acetic acid. After incubation in the same ice-cold solution for 30 minutes, the membrane was washed under pressure with successive ice-cold 10 ml portions of 0.1M sulfamic acid and enzyme coupling buffer.

EXAMPLE 11

Cyanogen Bromide Activation of Pyridyl Copolymer Membranes

The membrane of Example 7 containing pyridyl groups was activated by the successive passage therethrough of 50 ml of 0.1M NH$_4$OH, and two 50 ml volumes of p-dioxane, followed by the cycling of 20% (w/v) CNBr in p-dioxane for 10 minutes. The CNBr reagent was washed out with three 50 ml volumes of p-dioxane, followed by 50 ml of deionized water.

CT can be coupled to activated membranes at pH 8.5 in aqueous buffer. Solvent changes and membrane washings can be accomplished at 50 psi by the mounting of a membrane in a stainless steel pressure filtration funnel (Gelman Science). Enzyme activity of immobilized CT can be measured under continuous pumped-flow conditions at pH 8.5 with GPNA as a substrate. The protein loading of a membrane can be determined by ninhydrin analysis of an acid hydrolysate of a dried membrane, or quantitation of tryptophan in a base hydrolysate of a membrane.

As noted, proteins, such as alpha-chymotrypsin (CT), glucose isomerase (GI) and Protein A can be immobilized to the membranes after appropriate chemical activation. The most frequently used activation methods are: trichloro-s-triazine on the aryl amine membrane for the coupling of CT; diazotization on the aryl amine membrane for the coupling of GI. The weight loading for CT is about 6 to 12 percent with 40 to 65 percent retention of enzymatic activity. These results are typical of those obtained with ultrafiltration-type membranes. Membranes of higher porosity yeilded less loading but were of comparable activity.

The following examples illustrate coupling:

EXAMPLE 12

Chymotrypsin Coupling Procedures

CT was coupled to the TsT and the MDsT-activated membranes of Example 9 by the pressurized flow therethrough of 25 ml of ice-cold coupling buffer (0.1M Na HCO$_3$, pH 8.5, 0.1M NaCl), followed immediately by three passages of 15 ml of CT (10 mg/ml) in ice-cold coupling buffer. The membrane was then immersed and incubated in the same CT solution overnight at 4° C. Subsequently, the membrane was washed by the sequential pressurized flow therethrough of 75 ml of: coupling buffer; 1.0M ethanolamine, pH 8.0; 0.1M Tris.HCl, pH 9.4, 1.0M NaCl; 0.1M Na acetate, pH 4.0, 1.0M NaCl; 0.1M Na HEPES, pH 7.0, 0.1M NaCl, 0.02% NaN$_3$. The CT-coupled membranes were stored at 4° C. in the final wash buffer or in 1 mM HCl.

CT was attached to CNBr-activated pyridyl membranes and diazotized aryl amine membranes as described above, with the substitution of 0.5M NH$_4$Cl and 0.1M HEA in coupling buffer, respectively, for the ethanolamine solution.

EXAMPLE 13

Glucose Isomerase Coupling

GI was coupled to TST and to MDsT-activated membranes at pH 8.5 and pH 5.0, respectively. The former was identical to Example 12 except that it used 10 ml of GI solution at a concentration of 0.5 to 3.0 mg/ml. Coupling at the lower pH employed a buffer of 0.1M Na acetate, pH 5.0, 0.1M NaCl. Washing of GI-coupled membranes was done successively with 50 ml coupling buffer, 50 ml of 1.0M ethanolamine in coupling buffer, coupling buffer supplemented with 1.5M NaCl, 50 ml coupling buffer, and finally 50 ml of reaction buffer (0.1M Na maleate, pH 6.8, 0.1M NaCl). GI activated membranes were stored at 4° C. in reaction buffer supplemented with 0.02% NaN$_3$.

The coupling of GI to CNBr-activated pyridyl membranes and diazotized aryl amine membranes was comparable to that used for CT, in Example 9, but with a concentration of GI as mentioned above. Washing also was as mentioned in Example 12 with the appropriate substitution for the ethanolamine step.

EXAMPLE 14

Protein A and Bovine Serum Albumin Coupling

PA was coupled to pyridyl membranes via CNBr and to arylamine membranes via MDsT by passing through the membrane an 0.5 mg/ml solution of 0.1M NaHCO$_3$, 0.15M NaCl, pH 8.5; the filtrate was collected and recycled through the membrane five times. Membranes were then incubated overnight at 4° C. in the protein coupling solution, washed and stored at 4° C. in 0.1M HEPES, 0.15M NaCl, pH 7.0.

A control membrane to which a neutral, non-binding protein was coupled was also prepared, using pyridyl membranes via CNBr and also aryl amine membranes via MDsT. Control membranes were prepared to measure the non-specific adsorption or entrapment of protein on membranes. A protein which did not serve as an affinity ligand, in this case BSA, was coupled to an activated membrane. BSA was attached by passing a 3.0 mg/ml and a 20.0 mg/ml BSA solution in pH 8.5 coupling buffer through 13 mm and 47 mm membrane disks, respectively, and incubating as previously described.

The following examples illustrate the use of the coupled membranes in enzymatic conversion and affinity sorption:

EXAMPLE 15

Glucose Conversion

For glucose conversion, purified GI from *Streptomyces albus*, covalently immobilized as described in Example 13, with 10 percent weight loading and 50 to 70 percent retention of enzymatic specific activity was employed. The activity of membrane-bound GI was assayed at 70° C. in pH 6.8 maleate buffer containing 0.3M glucose, 7 mM MgSO$_4$, and 3 mM CoSO$_4$. Fructose formation was determined via cysteine-carbazole assay. The GI reactor containing a single 47 mm diameter membrane disk operated in a single pass flow mode at a flow rate of 0.5 ml/min and resulted in 10% conversion; up to 20% conversion was observed with higher flow rates. A Co$^{+2}$ concentration of 0.4 and 3.0 mM was necessary for optimal thermal stability of soluble and immobilized GI, respectively. The GI-membrane reactor had a half-life of about 150 hours. The $K_m$ and the $V_{max}$ for the immobilized GI were about 0.25M and 15 $\mu$mol/min-mg, respectively; these are slightly lower than and comparable to, respectively, those for soluble GI. When the flow rate was increased, a maximum level of activity was observed, at which diffusion control of the rate of reaction no longer existed. Diffusional limitations were insignificant at flow rates of at least 3 ml/min with a substrate concentration of 0.3M glucose.

For a continuous flow reactor at the chosen optimum cobalt concentration, a flow rate of 0.46 ml/min and a single-pass flow mode was operated continuously for 9 days. The half-life of the CFR was 150 hours. The reactor operated continuously at 0.45 ml/min in single-pass flow mode at 70° C. with maleate buffer containing 0.3M glucose.

The activity-pH profile of membrane-bound GI showed a quite broad peak, with 80% activity at pH 6.5 compared to 20% for the free enzyme, which suggests that practical operation at the more desirable, lower pH is possible with the membrane-bound enzyme. Peak activity is, in both cases, at pH 8.0.

The advantages of the membrane-bound GI system operated under pressure-driven conditions include the observation that the activity of the bound enzyme reached its peak at 85° C. with a rather flat plateau from 75°-90° C., while the native enzyme's activity peaked sharply at 70° C., was one-third of that at 65° C. and fell sharply at 80° C. Also, the pressure-driven reactor showed an activity which rose sharply with flow rate, reaching its maximum activity at quite reasonable flow rates and pressures depending on the hydraulic permeability of the membrane selected, so diffusion was not rate-limiting for this system. The intrinsic rate constants for the reversible conversion processes were found to agree rather well with those for the soluble enzyme. The properties of the bound enzyme systems showed overall advantages in terms of allowable pH and temperature ranges while being capable of rapid conversion rates.

The affinity sorption biospecific purification of biopolymer was also achieved, that of trypsin inhibitor and immunoglobulin G were effected by the forced flow of solutions containing these proteins through ultrafiltration membranes containing immobilized chymotrypsin or Protein A, respectively. Soybean trypsin inhibitor (STI) was also bound to chymotrypsin-containing membranes (0.75 g active enzyme/m$^2$) at pH 7 and 0.1 g/m$^2$ of protein eluted with urea at pH 2. Protein A binding species of IgG were analogously purified from serum albumin-IgG mixtures, with a yield of 0.5 g IgG/m$^2$ of membrane. The Protein A membranes were reuseable over a period of one month with no loss in binding activity. Flow through the pores of the membrane was laminar at the flow rates employed, and, the shear forces associated with such flow rates were shown not to be sufficient to disrupt an IgG-Protein A complex. Thus, the teachings of this invention can be compared to two common affinity chromatography purification systems employing bead systems, namely the binding of soybean trypsin inhibitor to immobilized a-chymotrypsin and the binding of the F$_c$ segment of immunoglobulin G to immobilized *Staphylococcus aureus* Protein A, The membranes of this invention showed that they could be used advantage for these purification and separation processes, and are a viable, highly efficient and rapid alternative to column methods.

For the affinity sorption purification-separation procedures, use was made of pyridyl membrane disks of 47 mm diameter reacted for 30 minutes with 0.1M CNBr in dioxane, followed by a wash with water to cleave the pyridine rings into two reactive aldehyde groups; also used were aryl amine membrane disks activated with 50 mM 2-methoxy-4,6-dichloro-s-triazine, 100 mM N,N-diisopropylethylamine in dioxane. CT was coupled as described in Example 12. The coupling of PA and BSA are described in Example 14.

The following example illustrates the affinity sorption of STI to immobilized CT:

EXAMPLE 16

Affinity Sorption of Soybean Trypsin Inhibitor to Chymotrypsin

For the affinity sorption of immobilized STI to CT, the enzymatic activity of immobilized CT was initially determined in a continuous flow GPNA assay. Membranes were then assayed for the binding of STI under convective flow conditions in a vacuum filtration system which consisted of a rotary vane vacuum pump, 125 ml filtration flasks, 47 mm diameter in-line polycarbonate filter holders (Gelman Sciences), syringe resevoirs, Tygon tubing outlets, and 5 ml polystyrene tubes placed inside the filtration flasks to collect eluates. Membranes were washed with 100 ml of binding buffer (50 mM Tris-HCl, 5 mM CaCl$_2$, pH 8.0) in a stainless steel filtration funnel at 50 psig before they were placed the in-line filter holders.

In the binding assay, 8 ml of a 0.30 mg/ml solution of tritiated STI in binding buffer was applied under a slight vacuum (2.7 psia), recycled through the membrane three times, and then allowed to incubate in the permeate overnight at 25° C. STI which may have bound non-specifically was eluted with 90 to 110 ml of wash buffer (50 mM Tris-HCl, 5 mM CaCl$_2$, 1.5M NaCl, pH 8.0) at 1.5 ml/min; the CT bound STI was eluted with 25 ml of elution buffer (8.0M urea, 0.1M NaCl, pH 2.0 with HCl) at 0.75 ml/min. Because of a decrease in the membrane flux upon the binding of STI, a higher vacuum (13.7 psia) was used throughout the wash and elution steps. Eluate fractions of 1 ml were collected and mixed with 5 ml of scintillation cocktail for counting on a Beckman Model LS 7000 liquid scintillation counter. Lastly, the enzymatic activity towards GPNA was remeasured and the protein loading of a membrane was determined by the assay of base hydrolysates for tryptophan.

The results are shown in Table 3.

TABLE 3

Binding of STI to Membranes Containing CT or a Non-Specific Ligand

| Membrane Ligand | STI Applied (mg) | mg of STI Eluted at pH 8.0 | mg of STI Eluted at pH 2.0 | STI Recovered (%) |
|---|---|---|---|---|
| CT | 3000 | 1893 | 164 | 73.5 |
| BSA | 2400 | 2160 | 26 | 94.2 |

STI was thus bound to competent molecules of immobilized CT by the forced convective flow of a STI solution through the membrane's pores. An excess of STI was provided during the binding stage so that the maximum amount of complex formation would result. Biospecifically bound STI was found to elute with urea at pH 2.0. Because of the high ratio of pore surface area to membrane volume and the large CT loading on a membrane, all binding occurred in a compact volume (a residence times of 7-14 sec. at the elution flow rates). Because of this compactness, the interface of pH change moves through the membrane with little dispersion; this is not the case for large columns where back-mixing occurs. This unique and advantageous feature of this membrane system allows the affinity bound material to elute off in a smaller volume, in this case 20 ml.

The affinity sorption procedure applied to the separation and purification of antibodies, including monocloved antibodies, made use of immobilized PA membranes as described in Example 17. Here IgG antibodies were employed. The elution of IgG from a PA-membrane based on the P(AN-4PV) copolymer of Example 14 was accomplished with a residence time 17-fold less than that required with a CT-membrane at the same flow rate. Since this complex does not involve a covalent bond, IgG is expected to dissociate faster than STI and elute in a smaller volume. This was observed for PA membranes. The excess IgG in the loading buffer was eluted in 10 ml of pH 7.0 buffer, while biospecifically bound IgG eluted in less than 5 ml of pH 3.0 buffer. Less than 1 mg of IgG was detected in the wash fractions prior to the change in pH. As was the case with STI, the highest concentration of IgG was found in the first acid fraction. Nevertheless, less than 20 ml was required to completely elute all non-bound and bound IgG.

EXAMPLE 17

Affinity Sorption of IgG to PA

Immobilized PA membranes from Example 14 were placed in 13 mm in-line filter holders and used in the vacuum filtration system of Example 15. The membranes were washed with IgG binding buffer (50 mM Na phosphate, 150 mM NaCl, pH 7.0) before passage of 2.5 ml of IgG binding buffer containing 0.4 mg/ml of $^3$H-IgG. After passage through the membranes three times at a flow rate of about 0.10 ml/min, the membranes were incubated in the final permeate overnight at 4° C. Then, the membranes were washed with 15 ml of binding buffer and affinity-bound IgG was eluted at pH 3 with 5 ml of IgG elution buffer (0.1M Gly-HCl, 1.5M NaCl, pH 3). Permeate fractions were collected and counted as previously described. Table 4 summarizes the results obtained with coupled PA membranes alongside these coupled BSA membranes for purposes of comparison.

TABLE 4

Binding of IgG to Membranes Containing PA or BSA.

| Membrane Type | Membrane Ligand | IgG Applied (mg) | mg of IgG Eluted at pH 7.0 | mg of IgG Eluted at pH 3.0 | IgG Recovered (%) |
| --- | --- | --- | --- | --- | --- |
| unsupported mAS-AN | PA | 651 | 476 | 40.9 | 79.3 |
| | PA | 1100 | 886 | 42.7 | 84.4 |
| | BSA | 651 | 582 | 2.5 | 89.8 |
| | BSA | 1100 | 970 | 4.2 | 88.6 |
| Unsupported 4VP-AN | PA | 1034 | 850 | 59.6 | 88.0 |
| | BSA | 1034 | 894 | 18.9 | 88.3 |
| Supported 4VP-AN | PA | 947 | 725 | 57.1 | 82.7 |
| | BSA | 947 | 781 | 39.8 | 86.7 |

Duplicate mAs-An membranes were assayed for IgG binding at two different concentrations. The tabulated entries are the average of two identical membranes. The membranes were washed with pH 7 buffer to remove non-specifically bound IgG and with pH 3 buffer to elute affinity bound IgG. The specially bound IgG was about 40 μg for both membrane types of the unsupported variety. The support makes for a substantial amount of non-specific sorption.

To demonstrate a practical use of these PA membranes, the affinity absorbancy of IgG out of a mixture of proteins was performed. If IgG is to be isolated directly out of serum without a prior separatory step, then large excess of serum albumin must not prevent IgG-PA complex formation. To show this, a mixture of BSA and human IgG with a 32:1 weight ratio of BSA to IgG was applied to PA membranes that were initially analysed for IgG binding from a homogeneous IgG solution. Following this, the membranes were washed extensively and analysed again for IgG bonding fron a homogeneous IgG solution. As long as sufficient IgG was present to saturate the PA ligands the binding capacity was substantially unchanged. When insufficient IgG was present for saturation and a large excess of BSA was present, there was some loss in IgG capacity probably due to loose, non-specific binding of BSA to PA and steric hinderance, but the IgG present was readily isolated from the mixture. A repeat uptake of pure and sufficient IgG showed the original PA capacity.

The strength and stability of the IgG-immobilized PA complex was also observed under forced convective flow with pH 7 buffer and with a protein solution through the membrane. It was found that the shear forces applied by pressure-driven affinity sorption cycles did not disrupt the PA-IgG complex nor did non-interacting proteins (BSA) compete with PA in eluting IgG from the membrane. Thus, the applicability of this system to blood processing was demonstrated.

For certain applications of the affinity sorption, it may be necessary to treat solutions or even fine suspensions which have in them so many large molecules or particles that the fine pore membranes customarily employed in ultrafiltration will not accommodate these materials. In other cases the actual complex to be formed is itself quite large and here also a fine pore membrane is not suitable simply on the basis of pore size.

Several solutions are available. The matrix copolymer membrane could be cast with a suitable porosity but this is often difficult to achieve while still maintaining adequate physical strength and there is the further disadvantage that many small pores of high adsorptive capacity are also formed to make for non-specific adsorption because they are not available for ligand coupling. Since the copolymers of this invention lend themselves very well to the coating of existing woven and nonwoven fabrics as well as polymeric surfaces, the preferred embodiment of this invention in these cases involves coating pre-existing fabric materials with the copolymer or coating an appropriate surface and then effecting the appropriate sequence of activation-coupling-sorption processes. Many fabrics including ones of polyester and nylon can be readily coated. With a judicious selection of solvents and the methodologies well known to those skilled in the art, coatings which are strongly adherent and cover the entire exposed surfaces are readily achieved. The speed of the sorption process is very high and no limitations of functions due to the presence of formed bodies obtain, particularly when solid surfaces are employed as in the classical "dipstick" procedure.

Example 17 describes another affinity sorption procedure, that which applies to the removal of fibronectin (FN) from a human plasma cryoprecipitate, as could be practiced in blood processing. FN is a non-enzymatic adhesive glycoprotein which binds strongly to certain substances and has itself a high molecular weight of 440,000 so it requires a highly available binding surface. Example 18 describes an affinity sorption system for FN.

EXAMPLE 18

Affinity sorption of Fibronectin By Coupled Gelatin Membrane

To an arylamine copolymer activated with TsT as described in Example 9 there can be coupled a gelatin fraction having an average MW of 16,000, carrying out the reaction at 35° C. to keep the gelatin in solution and provide for substantial binding of that ligand. An artificial cryoprecipitate, FN mixed with BSA, can be then passed through this immobilized gelatin filter employing a pH 7.4 buffer, following which the filter is washed with the same buffer. Then an eluting solution containing guanidine-HCl is used to desorbe the FN in concentrated solution.

Another application of affinity sorption to blood processing based on the specific reactions demonstrated by antibodies was demonstrated by the use of a coated fabric affinity sorption system for the binding of an antigen, in this case HSA, to an antibody, in this case Anti-HSA IgG or (ASG), to an immobilized PA filter. Here a three component complex is formed with PA bound directly by activation to the copolymer surface coating, itself treated with the antibody specific to the antigen HSA, and then the antigen removed from a complex mixture by affinity sorption. Depending upon the strength of the various complexes between PA and the antibody and between the antibody and the antigen, it may be necessary to effect a chemical coupling of the antibody to TA as is readily achieved by the familiar glutaraldehyde reaction.

EXAMPLE 19

Affinity Sorption by a PA membrane-ASG Complex of an Antibody

An immobilized PA filter was made by coating a fabric with polymer followed by the coupling of PA as described in Example 14, and then 3 ml of a 0.1 mg/ml solution of Rabbit anti-HSA IgG can be passed through to the PA as described in Example 16. At that point 3 ml of 0.25 mg/ml of tritiated HSA in IgG binding buffer is applied to the membrane followed by membrane washing, elution and counting as previously described. Substantial amounts of the antigen, in this case HSA, can be desorbed from the filter and concentrated thereby.

The problem of non-specific hydrophobic adsorption as interfering with the rate and sharpness of the separations to be achieved by affinity sorption processes has been documented earlier in this invention. Many means are available within the teachings of this invention for the amelioration or even elimination of this problem. AN copolymerizes also with a number of hydrophilic monomers including ones carrying the sulphonic acid group and others carrying the amide or similar hydrophilic groups. Monomers based upon acrylamide substituted with quarternary ammonium groups are also known. Terpolymers of AN together with a hydrophobic monomer and one of the three classes of copolymers employed for coupling could be prepared by those skilled in the art and these could serve to reduce the hydrophobicity of copolymers which are largely made up of AN. The introduction of hydrophilic monomers reduces the mechanical strength and increases the swelling of the resulting material, so there are several, basic limitations on the extent to which mixtures can be employed.

One of the techniques of this invention is the employment of specific combinations of polymers, coupling chemistries, ligands or enzymes, and the like, to accomplish specific processes to substantial advantage. In this light, it will be appreciated that the instant specification and the examples are set forth by way of illustration and not limitation and that various modifications and changes may be made without departing from the spirit and scope of the present invention.

We claim:

1. A process for producing a biologically active membrane comprising, in a water-miscible solvent forming a solution of a water insoluble copolymer of acrylonitrile with about 1 to 20.5 mole percent of at least one monomer selected from the group consisting of (a) an aminostyrene, (b) a vinyl pyridine and (c) an N-hydroxy-containing substituted-acrylamide, casting said solution to form a thin layer of solution, contacting said solution with water thereby to coagulate the copolymer into a film, washing away from the copolymer film the solution of solvent and water, activating the copolymer with (a) trichloro-s-triazine or by diazotization if the monomer is aminostyrene (b) cyanogenbromide if the monomer is vinyl pyridine or (c) trichloro-s-triazine if the monomer is an N-hydroxy-containing substituted-acrylamide, and then coupling to the activated copolymer a ligand selected from the group consisting of glucose isomerase, chymotrypsin and Protein A.

2. A process according to claim 1, including the further step of binding an antibody to Protein A coupled to the membrane.

3. A process according to claim 1, wherein the monomer is an aminostyrene.

4. A process according to claim 1, wherein the monomer is vinyl pyridine.

5. A process according to claim 1, wherein the monomer is an N-hydroxy-containing substituted-acrylamide.

6. A process according to claim 1, wherein the ligand is glucose isomerase.

7. A process according to claim 1, wherein the ligand is chymotrypsin.

8. A process according to claim 1, wherein the ligand is Protein A.

9. A biologically active membrane produced by the process of claim 1.

* * * * *